United States Patent [19]

Gulliya

[11] Patent Number: 5,674,870

[45] Date of Patent: Oct. 7, 1997

[54] ANTI-CANCER USES FOR BARBITURIC ACID ANALOGS

[76] Inventor: Kirpal S. Gulliya, 3818 Regent Dr., Dallas, Tex. 75229

[21] Appl. No.: 617,221

[22] Filed: Mar. 18, 1996

Related U.S. Application Data

[63] Continuation-in-part of Ser. No. 387,454, Feb. 13, 1995, abandoned.

[51] Int. Cl.$^6$ .................. A61K 31/515; A61K 31/505; C07D 239/66; C07D 239/62
[52] U.S. Cl. .................. 514/270; 544/299; 544/302; 544/319; 514/269
[58] Field of Search .................. 544/299, 302, 544/319; 548/300.1; 514/270, 390, 269

[56] References Cited

U.S. PATENT DOCUMENTS

| | | | |
|---|---|---|---|
| 3,148,189 | 9/1964 | Doran | 260/257 |
| 3,919,232 | 11/1975 | Barer | 260/257 |
| 3,919,427 | 11/1975 | Vida et al. | 424/254 |
| 4,292,312 | 9/1981 | Griffon | 424/176 |
| 5,312,919 | 5/1994 | Gulliya et al. | 544/302 |

FOREIGN PATENT DOCUMENTS

| | | |
|---|---|---|
| 622081 | 3/1963 | Belgium . |
| 745022 | 7/1970 | Belgium . |
| 2 003 994 | 7/1970 | Germany . |

OTHER PUBLICATIONS

Angst and Stabl, "Efficacy of Moclobemide in Different Patient Groups: A Meta–analysis of Studies," *Psychopharmacology*, 106:S109–S113, 1992.
Astwood et al., "Further Studies on the Chemical Nature of Compounds Which Inhibit the Function of the Thyroid Gland," *Endocrinology*, 37:456–481, Dec., 1945.
Beres et al., "Synthesis and Antibacterial Properties of Substituted Decylbarbituric Acids," *Journal of Pharmaceutical Sciences*, 63(3):469–471, 1974.
Beres et al., "Laboratory Note: Synthesis and Antibacterial Activity of High Alkyl Barbituric Acids," *Eur. J. Med. Chem.—Chimica Therapeutica*, 15(6):571–573, 1980.
Boyer and Feighner "Clinical Significance of Early Non–Response in Depressed Patients," *Depression*, 2:32–35, 1994.
Brown, D.J., "The Principal Synthetic Method," in *The Pyrimidines*, Interscience Publishers, a Division of John Wiley & Sons, Chapter II, Section 7, pp. 51–59, 1962.
Carter, Mary, Kathleen, "The History of Barbituric Acid," *Journal of Chemical Education*, pp. 524–526, Oct., 1951.
Carter & Coffey, "The Prostate: An Increasing Medical Problem," *The Prostate*, 16:39–48, 1990.
Cohen et al., "Changes in Axon Fluorescence During Activity: Molecular Probes of Membrane Potential," *J. Membrane Biol.*, 19(1–2):1–36, 1974.
Conrad and Guthzeit, "Ueber Barbitursäure–derivate," *Chem. Ber.*, 15:2844–2850, 1882.
Crumpacker II, Clyde S., "Molecular Targets of Antiviral Therapy," *Seminars in Medicine of the Beth Israel Hospital*, Boston, 321(3):163–172, 1989.
Deshpande and Datta, "Potential Antidiabetics 1–p–Toluene Sulphonyl–3 Alkyl (or Aryl) Barbituric Acid Derivatives," *Indian J. Appl. Chem.*, 35(4–6):145–146, 1972.
Dinno et al., "Potency of Barbiturates in Inhibition of Frog Gastric Secretion," *Proc. Soc. Exp. Biol. Med.*, 141:397–399, 1972.
Duvic, Madeleine, "Immunology of AIDS Related to Psoriasis," *The Journal of Investigative Dermatology*, 95(5):38S–40S, 1990.
Fischer and Merling, "Ueber eine neue Klasse von Schlafmitteln," *Die Therapie der Gegenwart*, 44:97–101, 1903.
Frazer, Alan, "Antidepressant Drugs," *Depression*, 2:1–19, 1994.
Gittes, Ruben F., "Carcinoma of the Prostate," *The New England Journal of Medicine*, 324(4):236–245, 1991.
Gorter, G.J.M.A., "Comparative Effectiveness of Barbiturates for Systemic Control of *Sphaerotheca Fuliginea* (Schlecht. Ex Fries) Poll.," *Phytophylactica*, 2:145–146, 1969.
Gysling and Schwarzenbach,, "Metallindikatoren II. Beziehungen zwischen Struktur und Komplexbildungsvermögen bei Verwandten des Murexids," *Helvetica Chimca Acta*, Chpt. 199, 32(5):1484–1504, 1949.
Haefely, W.E., "GABA and the Anticonvulsant Action of Benzodiazepines and Barbiturates," *Brain Research Bulletin*, 5(Suppl. 2):873–878, 1980.
Hahn et al., "A Calcium–sensitive Fluorescent Analog of Calmodulin Based on a Novel Calmodulin–binding Fluorophore," *The Journal of Biological Chemistry*, 265(33):20335–20345, 1990.
Hamburger and Salmon, "Primary Bioassay of Human Myeloma Stem Cell," *The Journal of Clinical Investigation*, 60:846–854, 1977.
Hirsch and Schooley, "Resistance to Antiviral Drugs: The End of Innocence," *The New England Journal of Medicine*, 320(5):313–314, 1989.
Kakemi et al., "Absorption and Excretion of Drugs," *Chem. Pharm. Bull.*, 15:1534–1538, 1967.

(List continued on next page.)

*Primary Examiner*—Mark L. Berch
*Assistant Examiner*—Bruck Kifle
*Attorney, Agent, or Firm*—Akin, Gump, Strauss, Hauer & Feld, L.L.P.

[57] ABSTRACT

Previously unknown anti-tumor, anti-infectious, immune system modulatory and anti-depressive properties of a family of barbituric acid derivatives are provided herein. Preferred derivatives are 4,6(1H, 5H)-pyrimidinedione, 1,3-dibutyldihydro-2thioxo; and 4,5,6(1H)-pyrimidinetrione, 1,3-dibutyldihydro-2thioxo. These compounds are effective for killing tumor cells, especially carcinoma (breast and prostate cancer), lymphoma and leukemia cells; for killing pathogenic organisms, especially viruses; for stimulating T cell formation and for alleviating symptoms of depression and are readily tolerated by the animal being treated.

16 Claims, No Drawings

OTHER PUBLICATIONS

Kamel, Mohsen M., "Barbituric Acid Derivatives," *Pharmazie*, 37:147, 1982.

Kauffman, George B., "Adolf von Baeyer and the Naming of Barbituric Acid," *J. Chem. Educ.*, 57:222–223, 1980.

Kessel and Morgan, "Research Note. Photosensitization with a Chlorin–Thiobarbiturate Conjugate," *Photochemistry and Photobiology*, 59(5):547–549, 1994. 1994.

Kline and Hunninghake, "T–Lymphocyte Dysregulation in Asthma," *Proc. Soc. Exp. Biol. and Med.*, 207:243–253, 1994.

Kreutzberger, Von A., "Tumorhemmende Wirkstoffe," *Arzneim.-Forsch./Drug Res.*, 28:1684–1687, 1978.

Menter and Barker, "Psoriasis in Practice," *The Lancet*, 338:231–234, 1991.

Meyer and Rollet, "Barbituric Acid and Barbiturates," in *Kirk–Opthmer Encycl. Chem. Technol.*, Second Edition, 3:60–77, 1964.

Miller, et at, "Thiobarbiturates," *J. Amer. Chem. Soc.*, 58:1090–1092, 1936.

Miller, et al., "Thiobarbiturates," *Science*, 81:616, 1935.

Pollard and Luckert, "Promotional Effect of Sodium Barbiturate on Intestinal Tumors Induced in Rats by Dimethylhydrazine," *J. Nat. Cancer Inst.*, 63(4):1089–1091 1979.

Pyles et al., "Spectrophotometric Measurement of Plasma 2–Thiobarbituric Acid–Reactive Substances in the Presence of Hemoglobin and Bilirubin Interference," *P.S.E.B.M.*, 202:407–419, 1993.

Rehse and Kapp, "3–(4–Amidinophenyl) –brenztraubensäuren analoge 5–Amidinobenzylbarbitursäuren," *Arch. Pharm.*, 315:346–353, 1982.

Robinson and Morgan, "Barbituric Acid Functionalized Porphyrins and Chlorins," *Tetrahedron Letters*, 34(23):3711–3714, 1993.

Sabata and Rout, "Influence of Structural Changes on Absorption in Merocyanines," *Sci. Ind. Res. (India)*, 21:227–229, 1962.

Salmon et al., "Quantitation of Differential Sensitivity of Human–Tumor Stem Cells to Anticancer Drugs," *N. Eng. J. Med.*, 298(24):1312–1327, 1978.

Schmidt, "Über Thiobarbitursäure-Methin-Farbstoffe," *Fette Seifer Anstrichmittel*, 61:881–886, 1959.

Sheob et al., "Studies in Possible Oral Hypoglycaemic Agents: Part VI–Synthesis of Some 2–& 4–Pyridylethyl Ureas & Thioureas & Some Barbiturates & Their Biological Activity," *Indian J. Chem.*, 5:145–146, 1967.

Singh and Behl, "1–Aryl–5–arylazo–3 (o–chlorophenyl) –2–thiobarbituric Acids as Potential Antineoplastic Agents.", *Indian J. Chem.*, 19:625–626, 1980.

Sladowska, "1,3–Dicyclohexyl–5–Alkyl–5–Aminomethylbarbituric Acids as Potential Antiinflammatory Agents," *Farmaco, Ed. Sci.*, 32(12):866–871, 1977.

Swinyard, "Sedatives and Hypnotics," in *Remington's Pharmaceutical Sciences*, 18th Edition, Mack Publishing Company, Chpt. 55, pp. 1057–1058 and 1063–1067, 1990.

Tabern and Volwiler, "Sulfur–Containing Barbiturate Hypnotics," *J. Amer. Chem. Soc.*, 57:1961–1963, 1935.

Tóth and Makleit, "Azido–Barbiturate, II," Acta Chimica Academiae *Scientiarum Hungaricae*, 107:147–153, 1981.

Vida et al., "Analgesics.3.Selected 1–Substituted and 1,3–Disubstituted 5–Propinoxy–5–(1–phenylethyl) barbituric Acids," *J. Med. Chem.*, 18(7):694–696, 1975.

Vida et al.,"Analgesics.2.Selected 5–Substituted 5–(1–Phenylethyl) barbituric Acids," *J. Med. Chem.*, 17(11):1194–1197, 1974.

Vida et al., "Analgesics.1.Selected 5–Substituted 5–Propionoxybarbituric Acids," *J. Med. Chem.*, 17(7):732–736, 1974.

Von Hoff et al., "Selection of Cancer Chemotherapy for a Patient by an In Vitro Assay Versus a Clinician," *J. Natl. Cancer Inst.*, 82:110–116, 1990.

Von Hoff et al., "Prospective Clinical Trial of a Human Tumor Cloning System, " *Cancer Res.*, 43:1926–1931, 1983.

Von Hoff et al., "Association Between Human Tumor Colony–Forming Assay Results and Response of An Individual Patient's Tumor to Chemotherapy," *Am. J. Med.*, 70:1027–1032, 1981.

Zawisza et al., "Syntheses and Pharmacological analysis of New Derivatives of Tetrahydro–[1, 3] –Thiazine and 2–Thiobarbituric Acid," *Arch. Immunol. Ther. Exp.*, 29:235–248, 1981.

Altman et al., "Glycemic agents associated with phospholipids (PL) and cholesterol (Chol) as growth inhibitors of implanted tumours*)," *Archiv für Geschwulstforschung*, 35/3, pp. 207–216, 1970.

Cherry et al., "The Effect of Growth Hormone, Insulin and Alloxan–Induce Diabetes on Carcinogenesis in the Genital Tract of Intact and Castrate Female Rats," *The British Journal of Cancer*, vol. XXV, No. 4, pp. 746–758, Dec., 1971.

Faye, Excerpt from *Principles of Medicinal Chemistry*, 4th Ed., Williams & Wilkins publisher, p. 167, 1995.

International Search Report for PCT/US96/01844, May 15, 1996.

Altman et al., "Glycemic agents associated with phospholipids (PL) and cholesterol (Chol) as growth inhibitors of implanted tumors," *Arch. Geschwulstforsch.*, 35/3, 1970 (abstract only).

ANTI-CANCER USES FOR BARBITURIC ACID ANALOGS

This application is a continuation-in-part application of U.S. Ser. No. 08/387,454 filed Feb. 13, 1995, abandoned and a continuation of PCT/US96/01844 filed Feb. 9, 1996.

FIELD OF THE INVENTION

This invention relates to new uses of a family of barbituric acid analogs for destroying cancer cells, inactivating pathogenic organisms, modulating the immune system, or alleviating symptoms associated with depression. A preferred embodiment of the present invention includes the use of 4,6(1H, 5H)-pyrimidinedione, 1,3-dibutyldihydro-2-thioxo for treating body tissues having cancer, the treatment being in vivo, ex vivo, or topical.

BACKGROUND OF THE INVENTION

Current treatment methods for cancer, including radiation therapy, surgery, and chemotherapy, are known to have limited effectiveness. For example, breast cancer annually kills tens of thousands of people in the United States; the numbers are surpassed only by the number of lung cancer deaths. A substantial increase in the number of new cases of prostate cancer has accompanied the aging of the American male population. One estimate suggests that between the years 1990 and 2000, cases of prostate cancer will increase by 90 percent and deaths from prostate cancer will increase by 37 percent (Carter and Coffey, 1990). Prostate cancer currently accounts for 12.3 percent of cancer deaths in men (Gittes, 1991).

Even with the implementation of educational programs designed to curb smoking and eating habits, cancer mortality rates will remain high well into the 21st century. The morbidity and mortality associated with cancer exacts an ever-increasing financial toll on an already overburdened health-care system. Clearly, effective agents that have cytotoxicity and specificity for cancer cells would fill a long and unmet need.

Although vaccines have been enormously successful in preventing many important viral diseases, there is still a pressing need for effective treatment of vital infections. Unfortunately, antiviral chemotherapy has lagged far behind antibiotic treatment for bacterial infections. Until recently, it was very difficult to find drugs that would inhibit viral functions without simultaneously damaging the closely related host cell mechanisms. With the recognizing of viral enzymes and proteins that can serve as molecular targets for drugs (Crumpacker, 1989), antiviral chemotherapy has become a practical reality. Unfortunately, the increasing clinical use of antiviral agents has begun to produce resistant viral strains (Hirsch and Schooley, 1989).

Depression is a serious public health problem with prevalence rates ranging from 5% to 21.3%. These illnesses are present in 3.6% to 7.9% of the population in a one-year period (Angst and Stabl, 1992). In the United States, these numbers translate into 8 million to 36 million adults at risk for depression in their lifetime. Depressed patients are about 20% more likely to attempt suicide and 15% of patients with major depression eventually die by suicide. Although a tremendous improvement in the treatment of these illnesses has been made, approximately 25% of depressed patients have a poor response to any particular antidepressant. Prior to treatment, it is not currently possible to predict which patient will respond. Also, the time for maximal therapeutic benefit to occur is at least one month or longer. Many currently available antidepressants have serious side effects. In view of the aforementioned factors, those of skill in this art have sought new antidepressants that elicit a faster response and have significantly reduced side effects.

The immune response is mediated by two different classes of lymphocytes: T cells, that develop in the thymus, are responsible for cell-mediated immunity; and B cells, that develop in bone marrow or fetal liver, produce antibodies. Thus, T cells are a major component of the immune system and, as such, they play a pivotal role in virtually all aspects of the immune system. The majority of T cells play a regulatory role in immunity, acting either to enhance (helper cells) or suppress (suppressor cells) the response of other white blood cells. T cells are involved in cell-mediated immunity, the production of cytokines, autoimmunity, tolerance, inflammation, and organ rejection. An imbalance of T cell function or their number results in serious disease states. For example, activated T helper cells and mononuclear cells as well as pro-inflammatory cytokines (Menter and Barker, 1991) are involved in psoriasis and arthritis and can be present as severe inflammatory dermatosis in patients with acquired immunodeficiency syndrome (Duvic, M., 1990). The immunodeficiency virus targets T helper cells and this infection causes a severe reduction in helper type T cells by killing them. The resulting imbalance in the number of helper T cells compromises the patient's overall immune system, rendering it ineffective even against common infections. On the other hand, hyperproliferation of T cells results in T cell leukemia. Further, T lymphocytes appear to play a central role in the pathogenesis of asthma (Kline and Hunninghake, 1994). Thus, there is an urgent need for drugs that cause a desirable modulation of T cells for the control of treatment of cancer, AIDS, arthritis, psoriasis and other diseases of the immune system.

The synthesis of barbituric acid starting from hydurilic and diliuric acid was first accomplished by Baeyer (1864). Barbital, a derivative of barbituric acid, was prepared by Conrad and Guthzeit (1882). The pharmacological properties of barbital were later described (Fisher and Mering, 1903; Baeyer, F. & Co., Ger. Pat. 247952, Mar. 04, 1911).

The barbiturates act as nonselective central nervous system depressants and are primarily used as sedative hypnotics and anti-convulsants in subhypnotic doses (Myer and Rollet, 1964). For example, the sodium salts of amobarbital, pentobarbital, phenobarbital, and secobarbital are presently available as prescription drugs. It is important to note that the basic structure common to these drugs, barbituric acid, in itself has no central nervous system activity. Central nervous system activity is obtained by substituting certain alkyl, alkenyl or aryl groups on the pyrimidine ring structure. The role of gamma-aminoisobutyric acid on anticonvulsant activity has been described (Hafeley, 1980).

Certain N-substituted barbituric acids with halogen atoms at C-5 display antiviral properties, including influenza virus (Ger. Offen 2003994, Belg. Pat. 622081). Other compounds such as 5-azidobarbituric acid and phenobarbital-papaverine act as an antispasmolytic (Toth et al., (Alkaloida Vegyeszeti Gyar), Hung, Teljes HU 19767 (Cl. C07D239/62), Apr. 28, 1981; Minelli, 1968; Canellas, Fr. M-3578 (Cl. A61K, C07d), Nov. 08, 1965; Saratikov et al., 1973; Spiridonova and Gol'tsev, 1976). N-arylbarbituric and N-arylthiobarbituric acids act as antiinflammatory agents (Pol. Pat. 106804; Pol. Pat. 110668; Zawisza et al., 1981; Sladowska, 1977).

Antitumor activity has been reported for 5-formylimidoylbarbituric acid derivatives (Meyer and Althnus, 1979; Kreutzberger, 1978); similar effects have been reported for N-phenyl-thiobarbituric acid under in vivo conditions (Singh and Behl, 1980). For 5,5-disubstituted barbituric acids, activities such as analgesic (Ger. Offen 1 817958; Vida et al., 1975, 1974a, 1974b; Jap. Pat. 20595), antidiabetic (Deshpande and Datta, 1972), antiepileptic (Wirth, 1975), antiinflammatory (Pol. Pat. 76936, Jap. Pat. 6807948), antigenic (Kuroiwa et al., 1980), antithyroid (Astwood et al., 1945), antithrombin (Rehse and Kapp, 1982), cardiotonic (Belonozhko et al., 1966), stimulation of plant growth (USSR Pat. 497006), diuretic (Ger. Offen. 2216619), fungicide and insecticide (Ger. Offen. 2719733; Ger. Offen., 2719777; U.S. Pat. No. 3,919,232; Gorter, 1970), herbicide (Ger. Offen. 2524578), inhibition of gastric secretion (Dinno et al., 1972; Kakemi et al., 1967), hypoglycemic (Shoeb et al., 1967), muscular relaxing (U.S. Pat. No. 3,919,427; U.S. Pat. No. 3,148,189; Bobranski et al., 1961), and hypotensive effects (Toth and Makleit, 1981) have been reported.

Only a few derivatives of thiobarbituric acid were prepared until 1935, when it was discovered that these compounds possess anesthetic properties (Miller et al., 1935; Tabern and Volwiler, 1935; Miller et al., 1936). Derivatives with a thiosemicarbazide group at the C-5 position and phenylhydrazones of 5-monoalkylbarbituric acids display antimicrobial properties (Kamel, 1982; Chemishev, 1979; Chemishev, 1981). The presence of allyl or n-decyl groups also confers antimicrobial properties (Beres et al., 1980; Beres et al., 1974).

Many barbituric acid derivatives such as thiobarbituric acid and its derivatives have also been used in the synthesis of dyes and pigments or intermediates in the preparation of dyes (Gysling, 1949; Schmidt, 1959; Sabata and Rout, 1962). Certain barbituric acid derivatives are photooxidation products of Merocyanine 540, and are reportedly useful as anticancer and antiviral agents (U.S. Pat. No. 5,312,919).

Alloxan has been used as a pretreatment for inhibiting the "take" of transplanted tumor cells (Altman and Spoladore, 1970); and has been used for inducing diabetes (Cherry and Glucksmann, 1971).

The prior art lacks reference to the barbituric acid analogs provided by the present invention as having anti-cancer, anti-pathogenic, immune-stimulating or anti-depressant properties. Because the diseases and other medical conditions that the present invention addresses are severe health problems and because known treatment procedures are not completely satisfactory, persons skilled in the art have searched for improvements.

SUMMARY OF THE INVENTION

The present invention seeks to overcome these and other drawbacks inherent in the prior art by providing a family of compounds that, heretofore, were not known to have properties helpful in treating cancer, infections, or immune-suppressed states. This family of compounds has barbituric acid as the root structure, however, members of the family provided herein do not possess narcotic activity or have central nervous system activity.

An embodiment of the present invention is a method of treating a host having a benign or malignant tumor, a viral infection, an immune system disorder, or depression associated with HIV-1. The method comprises the step of administering to the host a therapeutically effective amount of a barbituric acid analog having structure A, an optical isomer thereof, or a pharmaceutically acceptable salt thereof:

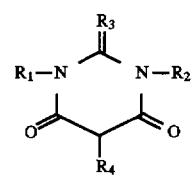

Preferably, $R_1$ and $R_2$ are independently hydrogen, or alkyl, alkoxy, polyether, alkylhalide, hydroxyalkyl, alkylamine, or alkylsulfhydryl having 1–6 carbon atoms, or aryl. The substituents of $R_1$ and $R_2$ may be linear or branched. Preferably, the alkyl is propyl, butyl or pentyl or isomers thereof; and most preferably, the alkyl is n-butyl. The halide of the alkyl halide may be chloride, bromide or iodide. The amine of the alkylamine may be primary, secondary or tertiary. The sulfhydryl may be a terminal—SH group or may be a disulfide linkage. One of ordinary skill in this art would realize, upon reading this disclosure, that the solubility and biodistribution of these compounds could be adjusted by varying the substituent R groups. $R_3$ is preferably O, S or Se. Alternatively, $R_3$ may be $C(CH_3)_2$. $R_4$ may be a doubly bonded oxygen or $R_4$ may be hydrogen. In the above-described method, $R_1$ and $R_2$ are most preferably n-butyl. Preferably, $R_3$ is S (thio) or O (oxo).

Compositions of matter of the present invention include a compound having structure A where $R_4$ is H, and $R_1$, $R_2$, and $R_3$ are as herein described; and a pharmaceutical formulation of a barbituric acid analog of structure A where $R_4$ is H, and $R_1$, $R_2$, and $R_3$ are as herein described together with a pharmaceutically acceptable carrier for intravenous, oral, or parenteral administration, or for ex vivo or in vitro use.

Preferred tumors for treatment using methods provided herein include sarcoma, carcinoma, lymphoma or leukemia. A preferred carcinoma is breast cancer or prostate cancer. A preferred host is a human host.

A further embodiment of the present invention is a method of inactivating pathogenic organisms comprising the step of contacting the pathogenic organism with an effective amount of a barbituric acid analog of the present invention. Pathogenic organisms that can be eradicated include the enveloped viruses and non-enveloped viruses. Viral infections treatable by the method of the present invention include herpes, hepatitis, or HIV infections.

An even further embodiment of the present invention is a method of increasing the number of T cells in an immunocompromised subject comprising administering to the subject an effective amount of a barbituric acid analog of the present invention.

A method of treating depression, particularly in an HIV-1 positive subject, is also an aspect of the present invention. The method comprises the step of administering to the subject an effective amount of a barbituric acid analog of the present invention.

In each of the above-described methods, the administering may be in vivo, in vitro or may be ex vivo. In vivo treatment is useful for treating diseases in an animal and the animal may be a human or a farm or a domestic animal, preferably the animal is a human; in vitro treatment is useful, for example, for purifying tissue cultures, for purifying culture medium; and ex vivo treatment is useful for purging body fluids, such as blood, plasma, bone marrow, and the like, for return to the body. Body tissue may be internal or external to an animal body, or, for example, may be the surface skin of the animal.

The effective amount is from about 0.001 mg/kg to about 2 or 3 g/kg for administering to a subject or, for ex vivo use, the range is from about 0.1 μg/ml to 2.0 g/ml.

Preferred analogs of barbituric acid for the herein described methods are 4,6(1H, 5H)-pyrimidinedione, 1,3-dibutyldihydro-2-thioxo, (compound C1, which is structure A where $R_1$ and $R_2$ are $CH_2CH_2CH_2CH_3$, $R_3$ is S and $R_4$ is H); and 4,5,6(1H)-pyrimidinetrione, 1,3-dibutyldihydro-2-thioxo (compound C2, which is compound C1 having a doubly bonded oxygen at the 5 position). The biological properties of these compounds, as they relate to anti-tumor effects, anti-infectious effects, modulation of the immune response, or anti-depressive properties have not heretofore been investigated. Thus, compound C1 was synthesized according to the previously published method (Robinson et al., 1993; Hahn et al., 1990; Cohen et al., 1974) and its biological properties were investigated. As a result of these studies, the present inventor provides herein previously unknown anti-tumor, anti-infectious, immune system modulatory and anti-depressive properties of a set of barbituric acid analogs.

The present invention provides a method of treating body tissues that are infected with tumors or other pathogenic biological contaminants, either in vivo, ex vivo, or on the surface of the body, such as skin. A preferred method comprises the steps of dissolving a barbituric acid analog of the present invention in a pharmaceutically acceptable carrier and administering the formulation in a therapeutically effective amount to the body tissues that are infected with tumors or other pathogenic biological contaminants and having an affinity for a barbituric acid analog of the present invention. A further preferred method includes oral administration of a barbituric acid analog of the present invention with or without first dissolving the compound in a pharmaceutically acceptable carrier. A pharmaceutically acceptable carrier may be in the form of a capsule, pill or as liquid, slurry, or gel. Accordingly, the object of the invention is to provide a barbituric acid analog of the present invention for interacting with and destroying or inhibiting the growth of tumors or other pathogenic biological contaminants infecting body tissues of an animal.

Thus, a solution of a barbituric acid analog of the present invention prepared in a pharmaceutically acceptable carrier and adjusted to the desired concentration can then be used for either in vitro or in vivo applications. For in vitro applications, a solution containing an effective amount of the therapeutic agent is administered to body tissue or cells outside the body (ex vivo), and, in particular, the body is a human body. The mixture containing a barbituric acid analog of the present invention and the tissues or cells to be treated are then incubated at an appropriate temperature for a desired duration of time. This application is useful, for example, for extracorporeal treatment of body tissues, such as human tissues to eradicate tumor cells or other pathogenic biological contaminants infecting such body tissues. In the in vivo application, a barbituric acid analog of the present invention is administered either orally, or a solution containing an effective amount of the agent is directly administered into the animal body, for example, parenterally or by injection. This application is useful, for example, for the treatment of an animal, such as a human, having a tumor or other pathogenic biological contaminant or for treatment of diseases of the immune system where the T cell population is low or for treatment of a human suffering from depression.

Another object of the present invention is to provide a barbituric acid analog of the present invention for administration into an animal body for modulation of one or more components of the immune system that is beneficial and desirable to the animal body, in particular, an increase in the number of T cell lymphocytes. Arthritis, psoriasis and other diseases of the immune system may be treated using the methods provided herein. Another object of the invention is to provide a barbituric acid analog for the treatment of depression, particularly in an HIV-1-positive subject.

The term "interact", as used herein, denotes the general phenomena of having a therapeutic compound adhere to, accumulate in, or associate with tumor cells or other pathogenic biological contaminants infecting a body tissue. The term "interact", as used herein, also denotes the general phenomena of having a therapeutic compound associate with or accumulate in or adhere to the components of the immune system causing its modulation.

As used herein, the terms "contact", "contacted", and "contacting", are used to describe the process by which an effective amount of a pharmacological agent, e.g., a compound provided by the present invention, is brought in direct juxtaposition with the target cell.

The term "pathogenic biological contaminants" is to be understood to include viruses, enveloped or not enveloped, prions, microorganisms, parasites, bacteria, and the like.

"Tumors" or "tumor cells" is understood to include among others: cancer of the bone and connective tissues; cancer of the eye; cancer of the brain; cancer of the skin; leukemias, lymphomas, myelomas, melanomas, carcinoma including breast cancer and prostate cancer, endometrial carcinoma, lung cancer, cervical cancer, pancreatic cancer, ovarian cancer, hepatic cancer, solid tumors, sarcoma, and the like.

The term "body tissue" as used herein is to be understood to include "body fluid", red blood cells, white blood cells, cryo precipitate from blood plasma, other plasma proteins, bone marrow, skin, cornea, organs and tissues from an animal or a human body, and the like.

The term "body fluids" as used herein is to be understood to include whole blood, any formed elements of the blood, blood plasma, serum, fluid containing such components, fluids from plasmapheresis, plasma fibrinogen, cryo-poor plasma, albumin, gamma globulins, semen, and other fluids introduced or intravenously injected into the body of a patient or animal using known administration techniques. The term body fluid is to be understood to include body fluid prior to, or after, physical as well as chemical fractionation, separation or freezing.

The term "external" or "ex vivo" as used herein is to denote outside the animal or human body.

The term "animal" as used herein is to denote a warm blooded animal including human, and domestic and farm animals.

The phrase "chemomodifying agent" as used herein is to denote an agent, such as a chemical or any other agent, that can potentiate, augment or increase the therapeutic efficacy of a therapeutic agent. Hence, a chemomodifying agent can be an additive and may synergize the therapeutic efficacy of a therapeutic agent.

The phrase "a therapeutically effective amount" as used herein is to denote the concentration or quantity or level of the therapeutic agent that can attain a particular medical end, such as a cure or control or destruction of the undesirable cells, such as tumor cells, or pathogenic biological contaminants, without producing unacceptable toxic symptoms.

The term "enveloped virus" is understood to be a virus that is encased within a modified host cell membrane. An exception is the pox-virus that produces its own envelope membrane. Among families of enveloped viruses are:

Herpesviridae, Iridoviridae, Poxviridae, Hepadnaviridae, Orthomyxoviridae, Paramyxoviridae, Rhabdoviridae, Bunyaviridae, Retroviridae, Nodaviridae, Togaviridae, Flaviviridae, Retroviridae, and Arenaviridae. Among common species or genera of such enveloped viruses are: herpes simplex virus; pox virus; human immunodeficiency virus; simian immunodeficiency virus; Epstein-Barr virus; and the like.

Among the families of non-enveloped viruses are: Parvoviridae, Papovaviridae, Adenoviridae, Picornaviridae, Caliciviridae, Reoviridae, and Coronaviridae. Among species or genera of such non-enveloped viruses are: parvovirus; papillomavirus; adenovirus; polioviruses; hantavirus; ebola virus; and others.

Among the parasites are Parasitic protozoa such as Kinetoplastida, Sarcodina, Apicomplexa, also from phyla Myxozoa, Microspora, Platyhelminthes, Trubellaria, Trematoda, Digenea, Anepitheliocystidia, Cestoidea, Nematoda, Trichurata, Dioctophymata, Oxyurata, and Spirurata. Also included are organisms that cause malaria, trypanosoma, schistosoma, teniasolium, teniasaginata, acanthamoeba, echinococcus and lyme disease.

Included in the bacteria are gram-positive and gram-negative bacteria. Other microorganisms that can be effectively eradicated by the method of the present invention include, but are not limited to: *Trypanosoma cruzi*, *Bacillus subtilis*, and *Streptococcus faecalis*.

The active compounds may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, time-release formulations, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The term "carrier" as used herein denotes a vehicle, a solution containing water, buffer, ethanol, serum, serum proteins, lipoproteins, artificial bio-membranes, liposomes, monoclonal antibodies, carbohydrates, cyclodextrans, organic solvents, or other pharmaceutically acceptable or compatible solutions. The carrier, or vehicle, may or may not dissolve a barbituric acid analog of the present invention, and may enhance delivery of the therapeutic agent into effective proximity to the target tumor cells or other pathogenic biological contaminants infecting the body or diseases of the immune system. The final carrier, or vehicle, used is pharmaceutically compatible in that it is relatively non-toxic to the normal cells and normal tissues and it does not react with the solute or therapeutic agent contained therein.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compounds, sucrose as a sweetening agent, methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Following long-standing patent law convention, the terms "a" and "an" mean "one or more" when used in this application, including the claims.

ABBREVIATIONS

C1—4,6(1H, 5H)-pyrimidinedione, 1,3-dibutyldihydro-2-thioxo or, more commonly called N,N'-dibutyl-2- thiobarbituric acid.

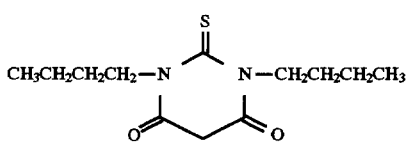

C2—4,5,6(1H)-pyrimidinetrione, 1,3-dibutyldihydro-2-thioxo.

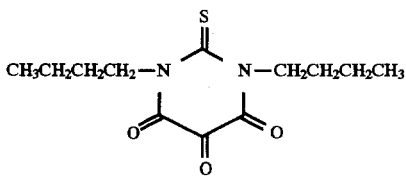

Compounds C4 and C5 have structure A where $R_1$ and $R_2$ are hydrogen (C4) and methyl (C5).

DETAILED DESCRIPTION OF THE PREFERRED EMBODIMENTS

The present invention provides novel methods for use of a family of barbituric acid analogs that are capable of killing, or inhibiting the growth of benign or malignant tumor cells or other pathogenic biological contaminants infecting body tissues, treating conditions of the immune system, or improving symptoms of depression. As demonstrated in the following examples, compounds C1 and C2 are powerful anti-tumor agents, particularly against carcinoma, such as prostate cancer or breast cancer, sarcoma, leukemia and lymphoma. The toxicity of compound C1 is provided in Example 7. Studies were also carried out to establish anti-viral, immunomodulatory and anti-depression properties of compound C1.

The following materials and methods are not to be construed as limiting.

Synthesis of Compound C1: 4,6(1H, 5H)-Pyrimidinedione, 1,3-dibutyldihydro-2-thioxo was synthesized, freeze dried and stored at room temperature for use in the following examples. The synthesis was carried out as described in Brown (1962) as follows: A 3-necked 2 liter flask fitted with a water condenser, gas inlet, and suba seal was purged with dry $N_2$. A freshly prepared solution of sodium ethyrate, prepared by slowly adding 2.5 g of Na to 50 ml EtOH at room temperature, was added to the flask. Diethyl malonate (17g, 110 mmol) was then added with vigorous stirring, followed by the addition of N,N'-dibutyl-2-thiourea (10 g, 53 mmol). The mixture was stirred vigorously under $N_2$ for 3 days. The mixture was cooled to room temperature, 50 ml of water was added carefully and ethanol was removed under reduced pressure. The remaining residue was poured into water (200 ml) and cooled in an ice/water bath. The solution was filtered to remove unreacted starting materials and acidified with dilute HCl. The resulting precipitate was collected by suction filtration, washed with water, and dried thoroughly to give a white solid. The yield was about 75%. Compound C1 was determined to be approximately 98% pure by TLC and NMR.

Synthesis of 4,5,6(1H)-pyrimidinetrione, 1,3-dibutyldihydro-2-thioxo, Compound C2: A sample of N,N'-dibutyl-thiobarbituric acid (10 g) was dissolved in toluene (100 ml) and dried $SeO_2$ (10 g) was added. A steady stream of air was passed through the solution, and the solution was heated to reflux for 1 h. After cooling overnight, the solvent was removed under reduced pressure and the residue was chromatographed on activated alumina using chloroform as eluant. The desired compound was isolated after evaporation of the solvent and examined for purity by TLC and NMR. Yield—6 g.

Two further analogs of C1 were synthesized and tested for toxicity for lymphoma cells. Analog C4 has structure A where $R_1$ and $R_2$ are hydrogen, $R_3$ is S and $R_4$ is H. Analog C5 has structure A where $R_1$ and $R_2$ are methyl, $R_3$ is S and $R_4$ is H.

Cell lines for the following examples were obtained from American Type Culture Collection (Rockville, Md.), and were maintained in recommended medium at 37° C. in a humidified atmosphere of 5% $CO_2$ in air.

In the following examples, tumor cells were treated with varying concentrations of compounds C1, C2, C4 or C5 dissolved in absolute ethanol. To limit any non-specific toxicity, the final concentration of ethanol was not allowed to exceed 0.5%. Stock concentrations of 5 mg/ml or 20 mg/ml were used. Viability of cells was determined in some studies by the trypan blue dye exclusion method. In other studies, cell viability/proliferation activity was determined by MTT assay by using a kit obtained from Promega, (Promega Corp., Madison, Wis. 53711). For this assay, a 100 μl cell suspension containing $5 \times 10^3$ monolayer cells or $1 \times 10^5$ suspension cells was placed in the wells of a 96-well microtiter plate. After overnight incubation, cells were treated with different concentrations of the test compound. Control wells received vehicle only. After 24, 48, 72 or 96 h of incubation, 50 μl of MTT dye solution was added. After 4 h of incubation at 37° C., 100 μl of solubilization/stop solution was added. After another h of incubation, cells were mixed using a multi-channel pipet and the absorption of the dye color was recorded at 570 nm using a plate reading absorption spectrophotometer.

Methods of in vitro assay, such as those disclosed in *Selected Methods in Cellular Immunology*, Eds. B. B. Mishell and S. M. Shiigi, W. H. Freeman and Company, San Francisco, Calif., 1980, and Plumb et al., *Cancer Res.*, 49:4435, 1980 were used. These references are incorporated by reference herein.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Cytotoxicity for Prostate and Breast Cancer Cell Lines

Human prostate cancer (PC-3 and DU-145 cell lines) and human breast cancer (MCF-7 and BT-20 cell lines) were treated with compound C1 or C2 for 24, 48, 72 or 96 h at 37° C. After the incubation period, viability of the cells was determined by MTT assay (Promega Corp., Madison, Wis. 53711). The resulting data are presented in Table 1.

TABLE 1

Effect of compound C1 and C2 on Prostate and Breast

| Cell Type | Cmpd C1 dose (μg/ml) | Percent cell kill | | | |
|---|---|---|---|---|---|
| | | 24 hr | 48 hr | 72 hr | 96 hr |
| PC-3 human | 50 | 61.7 ± 10.0 | 91.0 ± 3.6 | 100.0 | 100.0 |
| prostate | 100 | 88.7 ± 5.5 | 92.7 ± 1.2 | 100.0 | 100.0 |
| cancer | 150 | 90.5 ± 7.1 | 94.0 ± 5.3 | 100.0 | 100.0 |
| DU-145 human | 50 | 0 | 0 | 23.5 ± 4.5 | 26.2 ± 5.5 |
| prostate | 100 | 27.5 ± 6.4 | 52.2 ± 3.4 | 58.7 ± 2.1 | 64.0 ± 4.2 |
| cancer | 150 | 43.0 ± 2.9 | 71.0 ± 7.3 | 78.7 ± 3.4 | 82.5 ± 3.7 |
| MCF-7 human | 50 | 39.5 ± 10.5 | 67.5 ± 5.3 | 85.8 ± 3.8 | 97.8 ± 1.7 |
| breast | 100 | 57.3 ± 1.5 | 92.8 ± 4.9 | 88.0 ± 5.4 | 97.8 ± 1.7 |
| cancer | 150 | 87.8 ± 8.8 | 92.3 ± 5.3 | 84.5 ± 5.1 | 96.5 ± 2.5 |
| BT-20 human | 50 | 43.3 ± 4.1 | 65.5 ± 2.4 | 73.3 ± 2.9 | 100.0 |
| breast | 100 | 62.0 ± 7.9 | 91.3 ± 2.5 | 86.8 ± 3.6 | 100.0 |
| cancer | 150 | 94.0 ± 4.2 | 96.5 ± 2.4 | 86.0 ± 3.6 | 100.0 |

| Cell Type | Cmpd C2 dose (μg/ml) | Percent cell kill | | | |
|---|---|---|---|---|---|
| | | 24 hr | 48 hr | 72 hr | 96 hr |
| PC-3 | 100 | 32.7 ± 6.2 | 46.2 ± 4.1 | 51.5 ± 6.5 | 75.0 ± 1.0 |
| human | 150 | 47.0 ± 6.7 | 70.7 ± 6.0 | 77.7 ± 4.6 | 88.7 ± 3.2 |
| prostate cancer | 200 | 57.5 ± 3.5 | 81.5 ± 3.1 | 88.5 ± 5.2 | 95.0 ± 3.6 |
| DU-145 | 100 | 0.0 | 0.0 | 0.0 | 10.0 ± 6.1 |
| human | 150 | 0.0 | 4.2 ± 3.9 | 9.2 ± 5.3 | 25.2 ± 7.4 |
| prostate cancer | 200 | 0.0 | 20.0 ± 3.0 | 36.7 ± 2.1 | 43.7 ± 4.3 |
| MCF-7 | 100 | 9.0 ± 7.0 | 16.3 ± 4.8 | 33.3 ± 5.4 | 87.7 ± 0.6 |
| human | 150 | 26.3 ± 7.9 | 43.3 ± 7.3 | 61.0 ± 5.6 | 97.0 ± 0.8 |
| breast cancer | 200 | 40.0 ± 10.6 | 70.3 ± 7.8 | 81.3 ± 3.2 | 94.3 ± 2.1 |
| BT-20 | 100 | 29.8 ± 6.8 | 51.8 ± 1.9 | 57.5 ± 2.6 | 99.9 |
| human | 150 | 30.0 ± 4.4 | 50.0 ± 1.7 | 60.8 ± 2.8 | 99.9 |
| breast cancer | 200 | 30.3 ± 2.9 | 55.5 ± 8.9 | 68.5 ± 3.4 | 99.9 |

These data show that human prostate and breast cancer cells were susceptible to the cytotoxic action of both compounds C1 and C2. Compound C1 killed over 96% of PC-3 prostate and both breast cancer cell lines, and over 82% of DU 145 prostate cancer cells after a 96 h treatment at 150 μg/ml. Compound C2 killed over 94% of PC-3 prostate and both breast cancer cell lines, and over 43% of DU 145 prostate cancer cells after a 96 h treatment at 200 μg/ml. Cell kill in untreated controls (vehicle only) ranged from 5% to 15% for all experiments including those in subsequent examples.

EXAMPLE 2

Cytotoxicity for Lymphoma and Leukemia Cells

The Daudi human lymphoma cell line and the L1210 mouse leukemia cell line were treated with compound C1 or C2 for 24 or 48 h at 37° C. The viability of the cells was determined as in Example 1. Table 2 provides the resulting data.

TABLE 2

Effect of Compounds C1 or C2 on Leukemia and Lymphoma Cells

| Cell Type | C1 Dose (μg/ml) | % Cytotoxicity | |
|---|---|---|---|
| | | 24 hr. | 48 hr. |
| Daudi human lymphoma | 50 | 91.3 ± 4.6 | 99.9 |
| | 100 | 93.3 ± 4.9 | 99.9 |
| | 150 | 94.0 ± 4.9 | 99.9 |
| L1210 mouse leukemia | 50 | 81.2 ± 4.1 | 99.0 |
| | 110 | 93.5 ± 3.1 | 99.9 |
| | 150 | 89.2 ± 3.2 | 99.9 |

| Cell Type | C2 Dose (mg/ml) | % Cytotoxicity | |
|---|---|---|---|
| | | 24 hr | 48 hr |
| Daudi human lymphoma | 100 | 57.5 ± 3.0 | 41.5 |
| | 150 | 81.3 ± 4.0 | 92.0 |
| | 200 | 93.2 ± 3.3 | 88.0 |
| L1210 mouse leukemia | 100 | 33.2 ± 2.0 | 29.0 ± 3.5 |
| | 150 | 50.0 ± 4.1 | 53.7 ± 2.5 |
| | 200 | 58.7 ± 2.6 | 72.5 ± 2.4 |

These results show killing of human lymphoma Daudi cells and mouse leukemia L1210 cells with compounds C1 and C2. Exposure to compound C1 resulted in over 99% killing of these cells after a 48 h incubation period at all concentrations tested. Exposure to compound C2 resulted in over 90% and 58% killing of these cells, respectively, after a 24 h incubation period at 200 μg/ml. Compounds C4 and C5 were also tested for toxicity against human lymphoma Daudi cells. Incubation at 150 µg/ml produced a cell kill of less than 20%, indicating that these derivatives are less effective than compounds C1 or C2.

From the data presented herein, it is apparent that the methods of the present invention include near total destruction of various tumor cells.

EXAMPLE 3

Inhibition of Clonogenic Growth of Breast Cancer Cells

The effect of compound C1 on clonogenic human breast tumor cells was investigated. To assay clonogenic tumor cells, human breast cancer MCF-7 adenocarcinoma cells ($1\times10^3$ cells per flask for control and $5\times10^3$ cells for treatment groups) were plated and, after 24 h of incubation at 37° C. in a humidified atmosphere of 5% $CO_2$ and air, these cells were treated with 20 µg/ml, 40 µg/ml or 80 µg/ml of compound C1. After additional incubation periods of 24 h and 48 h, cells were washed to remove the drug and were allowed to grow at 37° C. in a $CO_2$ incubator. After 10 days, colonies consisting of 50 or more cells were counted. The resulting data are provided in Table 3.

TABLE 3

Effect of C1 on the Clonogenic Growth of Human Breast Cancer MCF-7 Cells

| C1 Dose (µg/ml) | No. of Colonies (Mean ± S.D.) | | Percent Reduction |
|---|---|---|---|
| | 24 hr | 48 hr | |
| 0 | 158.5 ± 12.2 | 158.5 ± 12.2 | 0 |
| 20 | 24.5 ± 7.8 | 24.5 ± 6.1 | 84.5 |
| 40 | 13.5 ± 5.1 | 11.7 ± 1.2 | 92.6 |
| 80 | 3.0 ± 2.2 | 0 ± 0 | 99.99 |

Compound C1 caused a virtually complete elimination of tumor cell clonogenic growth under the conditions employed.

EXAMPLE 4

Cytotoxicity for Human Prostate Tumors Transplanted into Mice

The activity of compound C1 in vivo against human DU-145 prostate tumors transplanted into athymic mice is demonstrated in the present example.

Male athymic BALB/c nude-nu mice (6–8 weeks old, 18–22 g each) were purchased from Harlan Sprague-Dawley, Inc. (Indianapolis, Ind.) and maintained in a germ-free environment. The mice had free access to sterile food and water. Human prostate DU-145 cells ($1\times10^7$) were transplanted subcutaneously into athymic mice. Solid tumors appearing after 30 days were cut into small pieces ($2\times2$ mm) and transplanted into native mice. Treatment of three prostate tumor bearing animals was initiated the next day by oral feeding of 400 mg/kg of compound C1 suspended in polyethylene glycol. The treatment schedule consisted of a single dose on alternate days. The control group of animals (3 mice) received vehicle only. After 18 doses of treatment, palpable prostate tumors in the treated group could not be detected, whereas tumors grew to an approximate tumor volume of 20 $cm^3$ in the control group. At this point, the treatment was terminated and animals were kept under observation for the regrowth of prostate tumors. As of 5 months posttreatment, there were no signs of tumor regrowth while only one control animal bearing prostate tumor was alive at that time point. During the course of this study, side effects such as weight loss, diarrhea or any signs of discomfort in the treated group of animals were not observed, indicating that compound C1 is readily tolerated. The results after an 18 dose treatment are presented in Table 4.

TABLE 4

Effect of Compound C1 on the Growth of DU-145 Human Prostate Tumors

| Treatment Group | Dose | Animal Weight (g) | Tumor Area ($cm^2$) | Tumor Volume ($cm^3$) | % TGI |
|---|---|---|---|---|---|
| Control | Vehicle only | 28.5 | 19.90 ± 7.1 | 20.64 ± 7.01 | |
| C1 | 400 mg/kg | 29.3 | 0.0 | 0.0 | 99.0 |

% TGI indicates percent tumor growth inhibition, calculated by using the formula % TGI = 100 (1 − $V_t/V_c$), where $V_t$ and $V_c$ are the mean volumes of the treated and control tumors, respectively.

These results show that even after an 18 dose treatment, palpable tumors were not detectable in treated animals. In addition, regrowth of treated tumors did not occur for a period of 5 months. No observable side effects, such as weight loss or lethargy, were observed in treated animals. In contrast, tumors grew rapidly to an average tumor volume of 20.64 $cm^3$ in untreated animals. These results clearly show that compound C1 is an effective antitumor agent in vivo and that it is readily tolerated.

Similar experiments were carried out where implanted human prostate tumors ($2\times2$ mm) were allowed to become established. Eight days later, the tumor size was≈$5\times5$ mm. Treatment was initiated which consisted of intramuscular injections of C1 (100 mg/kg) given on alternate days. After 5 weeks of treatment, tumors were not detectable by palpation in 2 of 3 animals. In the third animal, further tumor growth essentially did not occur since the tumor was $6\times5.5$ mm in size. Untreated control mice (n=3), had tumors at 5 weeks of average size of $10\times9$ mm.

EXAMPLE 5

Effect of C1 on Human Fibrosarcoma HT-1080 cells

Human fibrosarcoma cells were cultured in Minimum essential medium (Eagle) with non-essential amino acids and Earls balanced salt solution supplemented with 10% heat-inactivated fetal bovine serum. Cells ($5\times10^3$ in 0.5 ml of growth medium) were plated in 16 well plates and incubated at 37° C. in a humidified atmosphere of 5% $CO_2$ in air for 24 h. Cells were then treated with different doses of C1. Control wells received vehicle only (<0.5% ethanol in saline). After further incubation periods of 24 and 48 h, the viability of cells was determined by trypan blue dye exclusion method. The results are provided in Table 5.

TABLE 5

Effect of C1 on Human Fibrosarcoma HT-1080 cell[a]

| Time | Percent survival | | | | |
|---|---|---|---|---|---|
| (h) | Control | 25 µg/ml | 50 µg/ml | 100 µg/ml | 150 µg/ml |
| 24 | 92.3 ± 3.1 | 0.03 ± 0.03 | 0.03 ± 0.03 | 0 | 0 |
| 48 | 92.4 ± 3.1 | 0 | 0 | 0 | 0 |

[a]Control cells were treated with vehicle (0.5% ethanol in saline) only.

Virtually all fibrosarcoma cells were killed at 24 h at doses of 100 and 150 µg/ml. At a dose of 50 µg/ml, over 92% of the cells were killed. At 48 h, virtually all fibrosarcoma cells were killed even at the lowest dose of 25 µg/ml tested. In control wells, approximately 8% cells were killed at the highest dilution of solvent control. These results show that human fibrosarcoma cells are very susceptible to the cytotoxic action of C1.

EXAMPLE 6

C1 Efficacy as Determined by Human Tumor Cloning System

Through the initial work of Hamburger and Salmon (1977 a,b), it is possible to culture human tumors using a two-layer soft agar system. This culture system, called the human tumor cloning system, was initially utilized to select the most appropriate anticancer agent for an individual patient's tumor. Later, it was demonstrated that if a patient's tumor was sensitive to a drug in vitro, the chance of that patient responding clinically to the drug was 81%, while if the patent tumor was resistant to the drug in vitro, the chance of the patient not responding to the drug was 93% (Salmon, 1978). In an in vitro-in vivo correlation study involving 800 patients retrospectively, it was determined that the true positive rate for this assay was 70%, while the true negative rate for the assay was 98% (Von Hoff et al., 1981). In a more recent prospective clinical trial of the cloning system involving 604 patients, the percent true positive for the assay was 64%, while the percent true negative for the assay was 86% (Von Hoff et al., 1983). These studies have demonstrated that in vitro predictive assays can improve the response rate of patients. This system was used to study the response of compound C1 for breast cancer and non-small cell lung carcinoma.

Collection and preparation of tumor cells: After obtaining informed consent in accordance with federal and institutional guidelines, malignant effusions, ascites and bone marrow aspirates containing tumor cells as well as solid tumor specimens were collected from patients undergoing procedure carried out as a part of their diagnostic workup or as part of treatment for their disease. Solid tumors or lymph nodes were minced into 2 to 5 mm fragments in the operating room and immediately placed in McCoy's Medium 5A (Gibco, Grand Island, N.Y.) containing 10% heat-inactivated newborn calf serum plus 1% penicillin/ streptomycin. Within four h, these solid tumors were mechanically disassociated with scissors, forced through No. 100 stainless steel mesh, through 25 gauge needles, and then washed with McCoy's medium as previously described (Hamburger & Salmon, 1977, a,b; Salmon, 1978, Von Hoff et al., 1981, 1983, 1990). Ascites, pleural, pericardial fluids and bone marrow were obtained by standard techniques. The fluid or marrow was placed in sterile containers containing 10 units of preservative-free heparin per ml of malignant fluid or marrow. After centrifugation at 150×g for 10 minutes, the cells were harvested and washed with McCoy's medium plus 10% heat inactivated fetal calf serum. The viability of cell suspensions thus obtained was determined with trypan blue.

Tumor cells to be cloned were suspended in 0.3% agar in enriched CMRL 1066 medium (Gibco, Grand Island, N.Y.) supplemented with 15% heat-inactivated horse serum, penicillin (100 units/ml), streptomycin (2 mg/ml) glutamine (2 mM), insulin (3 units/ml), asparagine (0.6 mg/ml), and HEPES buffer (2 mM). Different concentrations of compound C1 were added to the above mixture and cells were plated in 35 mm petri dishes in a top layer of agar over an underlayer of agar to prevent growth of fibroblasts. Three plates were prepared for each data point and incubated at 37° C. After an incubation period of 14 days, plates were removed and the number of colonies were counted in each plate. The number of colonies (defined as>50 cells) formed were compared in drug treated and untreated (control) plates and the percent colonies surviving at each drug dose tested was then calculated as a percentage of control.

TABLE 6

Activity of C1 in a Human Tumor Cloning System

| Tumor type | # responsive tumors/total # evaluated | | |
|---|---|---|---|
| | 75 µg/ml | 100 µg/ml | 125 µg/ml |
| Breast | 3/8 | 4/8 | 6/8 |
| Lung Carcinoma (non-small cell) | 0/1 | 1/1 | 1/1 |

In the above table, a responsive tumor is defined as one where at least 50% inhibition of tumor colony formation occurred. The data indicate a very high probability of successful inhibition of breast tumor and lung carcinoma with compound C1.

EXAMPLE 7

In Vivo Toxicity

In order to determine the in vivo toxicity of compound C1, BALB/c mice were orally administered a single escalating dose of C1. A single escalating dose of the test drug is a procedure where a dose is administered to a group of mice (in this case n=3). If toxicity is not elicited, the next higher dose is given to a fresh group of mice and so on until toxicity is observed.

In preliminary repeat dose studies, a suspension of C1 in polyethylene glycol (C1 is mixed with a 2.5% solution of polyethylene glycol and homogenized in a sterile dounce homogenizer until it flows freely through a 22×1½" with 1¼ mm ball feeding needle) was administered orally to a group of three BALB/c mice.

A daily dose of 400 mg/kg given for 10 days was easily tolerated and all animals survived the treatment. At the dose of 800 mg/kg, one animal died on day three and another died on day 10. At the dose of 1000 mg/kg, one animal died on day 2, another on day 5 and a third animal died on day 10. At the dose of 1200 mg/kg, all animals died on day 3.

A single dose of up to 1200 mg/kg was easily tolerated. However, a single dose of 2000 mg/kg was lethal. A parenteral dose may be from about 1 µg/kg to about 500 mg/kg.

EXAMPLE 8

Anti-Viral Activity

The anti-viral activity of compound C1 was determined as follows; a stock of Herpes simplex virus (HSV) was mixed with different concentrations of compound C1 and incubated for 24 h at 37° C. The control sample received vehicle only. After the incubation period, samples were serially diluted and 0.1 ml of each dilution and the undiluted samples were inoculated into monolayers of Vero cells (African green monkey kidney cells). Overlay medium was added and the monolayers were incubated at 37° C. After 3 days of incubation, the overlay medium was removed, and the monolayer cells were fixed with methanol and treated with Giemsa stain. Plaques were counted and results are shown in Table 7.

TABLE 7

Effect of Compound C1 on the Inactivation of Herpes Simplex Virus

| Dose of C1 | *PFU/ml | % Inactivation | Log Reduction |
|---|---|---|---|
| 0 | $7.1 \times 10^5$ | 0.0 | 0.0 |
| 30 µg/ml | $2.1 \times 10^5$ | 70.4 | 0.53 |
| 60 µg/ml | $1.5 \times 10^5$ | 78.9 | 0.68 |
| 120 µg/ml | $6.5 \times 10^5$ | 99.1 | 2.04 |
| 150 µg/ml | $7.5 \times 10^5$ | 99.9 | 3.00 |

*PFU = Plaque forming units.

These results show that a near complete inactivation (99.9%) of Herpes simplex was obtained in a dose-dependent manner.

In a further study, cell free human immunodeficiency virus (HIV-1) was treated with a range of concentrations of compound C1. After 2 h at 37° C., treated and control HIV-1 samples were added to the indicator MT-4 cells (cultured human T cells) in the presence of 2 µg/ml POLYBRENE™ for 2 h. After washing, MT-4 cells were cultured in the presence of drug-treated or control (untreated) HIV-1. Cell viability of MT-4 cells was determined by the trypan blue dye exclusion method. The results are presented in Table 8.

TABLE 8

Effect of Compound C1 on the inactivation of cell free human immunodeficiency virus

| Cell Type | Dose (µg/ml) | % Inactivation Day 7 |
|---|---|---|
| MT-4 cells (uninfected) | 0 | 0 |
| MT-4 + HIV-1 | 0 | 0 |
| MT-4 + HIV-1 | 75 | 7.7 |
| MT-4 + HIV-1 | 100 | 34.1 |
| MT-4 + HIV-1 | 125 | 62.6 |

These results show that even a 2 h period of treatment at 125 µg/ml provided a 62% inactivation of the virus on day 7 as compared to essentially complete killing of cells by the untreated HIV-1 in the control culture. Under these conditions, the drug doses were not toxic to the MT-4 cells.

EXAMPLE 9

Stimulation of the Immune System and Treatment of Depression

The effect of compound C1 on the modulation of T cells was studied. After obtaining informed consent, three human HIV-1 positive volunteer subjects received compound C1 at a dose of 4.3 mg/kg for a period of 15 days. Blood samples were drawn before and after on day 15 or 30 from the initiation of treatment for regular CBC profile. Data from one subject showed that the T cell count increased from 425 to 720. The normal range of T cells is 650–1330. These subjects also reported an alleviation from lethargy, depression and an increased appetite, feeling of being happy, and desire to live.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Altman, R. F. A. and L. G. Spoladore, *Archiv für Geschwulstforschung* 36:3, 207–216, 1970.
Angst, J. and Stabl, M., *Psychopharmacology*, 106:S109–S101, 1992.
Astwood et al., *Endocrinology*, 37:456, 1945.
Baeyer, A., *Ann.*, 131:291, 1864.
Belg. Pat. 622081, Mar. 4, 1963.
Belonozhko et al., *Fiziol. Akt. Veshchestva, Akad. Nauk Ukr. SSR, Respub. Mezhvedom. Sb.*, 10, 1966.
Beres, J. A. et al., *J. Pharm. Sci.*, 63:469, 1974.
Beres, J. A. et al., *Eur. J. Med. Chem.–Chim. Ther.*, 15:571, 1980.
Bobranski et al., *Arch. Immunoo. Therap. Doswiadczalnej*, 9:1, 1961.
Brown, D. J., *The Pyrimidines*, Heterocyclic Compounds, Interscience Publishers, pp. 51–59, 1962.
Canellas, Fr. M-3578 (Cl. A61K, C07d), Nov. 8, 1965.
Carter, H. B. and Coffey, D. S., *Prostate*, 16:39, 1990.
Carter, M. K., *J. Chem. Educ.*, 524, 1951.
Chemishev, B. and Kantardzhiev, V., *Doki. Bldg. Akad. Nauk.*, 34:213, 1981.
Chemishev, B., Farmatsiya (Sofia), 29:6, 1979.
Cherry, C. P. and A. Glucksmann, *Brit. J. Cancer*, 25:4, 746–758, 1971.
Cohen, L. B. et al., *J. Membrane Biol.*, 19(1–2):1, 1974.
Conrad, M. and Guthzeit, M., Chem. Ber., 15:2844, 1882.
Crumpacker, II, C. S., *N. Engl. J. Med.*, 321:163, 1989.
Deshpande and Datta, *Indian J. Appl. Chem.*, 35:145, 1972
Dinno et al., *Proc. Soc. Exp. Biol. Med.*, 141:397, 1972.
Duvic, M., *J. Invest. Dermatol.*, 95:38S, 1990.
Fisher, E. and Mering, J., *Ther. Gegenwart*, 44:97, 1903.
Ger. Pat. 247952, Mar. 4, 1911.
Ger. Offen 2003994, Jul. 30, 1970.
Ger. Offen. 2216619, Oct. 18, 1973.
Ger. Offen. 2524578, Dec. 11, 1975.
Ger. Offen. 2719733, Nov. 17, 1977.
Ger. Offen., 2719777, Nov. 24, 1977.
Gittes, R. F., *N. Engl. J. Med.*, 324:236, 1991.
Gorter, *Phytophylactica*, 2:145, 1970.
Gysling, H. and Schwarzenbach, G., *Helv. Chim. Acta.*, 32:1484, 1949.

Hafeley, W. E., *Brain Res. Bull.*, 5:873, 1980.
Hahn, K. et al., *J. Biol. Chem.*, 265(33):20335, 1990.
Hamburger, A. W. and Salmon, S. E., *J. Clin. Invest.*, 60:846–854, 1977a.
Hamburger, A. W. and Salmon, S. E., *Science.*, 197:461, 1977b.
Hirsch, M. S., and Schooley, R. T., *N. Engl. J. Med.*, 320:313, 1989.
Kakemi et al., *Chem. Pharm. Bull.*, 15:1534, 1967.
Kamel, M. N., *Pharmazie*, 87:147, 1982.
Kauffman, G. B., *J. Chem. Educ.*, 57:222, 1980.
Kline, J. N., and Hunninghake, G. W. *Proc Soc. Exp. Biol. and Med.* 207:243, 1994.
Kreutzberger, *Arzneim-Forsch.*, 28:1684, 1978.
Kuroiwa et al., Jpn. Kokkai Tokkyo Koho 80, 112, 568 (Cl. G01N33/54), Aug. 30, 1980.
Jap. Pat. 20595, Oct. 5, 1960.
Jap. Pat. 6807948.
Menter, A. and Barker, J. N. W. N., *Lancet* 338, 231, 1991.
Meyer and Althnus, *Symp. Med. Hoechst*, 14:373, 1979.
Miller, E. et al., *J. Amer. Chem. Soc.*, 58:1090, 1936.
Miller, E. et al., *Science*, 81:616, 1935.
Minelli, *Biol. Chim. Farm.*, 107:446, 1968.
Myer, R. and Rollet, M., Barbituric Acid and Barbiturates, In Kirk-Opthmer Encycl. Chem. Technol. ed. 2, Vol. 3, p. 60, 1964.
Naito, Ger. Offen 1 817958 (Cl. C07D), Jun. 26, 1975.
Partington, J. R., A history of chemistry, Vol. 4, p. 777, Macmillan & Co., Ltd. London 1964.
Pol. Pat. 106804, Jan. 31, 1980.
Pol. Pat. 76936, Jul. 15, 1975.
Pol. Pat. 110668, Jul. 31, 1981.
Pollard and Luckert, *J. Nat. Cancer Inst.*, 63:1089, 1979.
Rehse and Kapp, *Arch. Pharm.*, 315:346, 1982.
Robinson, B. C. and Morgan, A. R., *Tetrahedron Lett.*, 34(23):3711, 1993.
Sabata, B. K. and Rout, M. K., *J. Sci. Ind. Res.* (India), 21:227, 1962.
Salmon, S. E. et al., *N. Eng. J. Med.*, 298:1312, 1978.
Saratikov et al., *Izv. Sib. Otd. Nauk SSR Biol. Nauk.*, 2, 147, 1973.
Schmidt, H., *Fette Seifer Anstrichmittel*, 61:881, 1959.
Shoeb et al., *Indian J. Chem.*, 5:145, 1967.
Singh and Behl, *Indian J. Chem.*, 19:625, 1980.
Sladowska, *Farmaco, Ed. Sci.*, 32:866, 1977.
Spiridonova and Gol'tsev, *Zh. Org. Khim.*, 46:2186, 1976
Tabern, D. L. and Volwiler, E. H., *J. Amer. Chem. Soc.*, 57:1961, 1935.
Toth and Makleit, *Acta Chim. Acad. Sci. Hung.*, 107:147, 1981.
Toth et al., (Alkaloida Vegyeszeti Gyar), Hung. Teljes HU 19767 (Cl. C07D239/62), Apr. 28, 1981.
U.S. Pat. No. 3,148,189, Sep. 8, 1964.
U.S. Pat. No. 3,919,427, Nov. 11, 1975.
U.S. Pat. No. 3,919,232, Nov. 11, 1975.
U.S. Pat. No. 5,312,919, May 17, 1994.
USSR Pat. 497006, Dec. 30, 1975.
Vida et al., *J. Med. Chem.*, 18:694, 1975.
Vida et al., *J. Med. Chem.*, 17:1194, 1974a.
Vida et al., *J. Med. Chem.*, 17:732, 1974b.
Von Hoff, D. D. et al., *Am. J. Med.* 70:1047, 1981.
Von Hoff, D. D. et al., *Cancer Res.* 3:1926–1931, 1983.
Von Hoff, D. D. et al., *J. Natl. Cancer Inst.* 82:110–116, 1990.
Wirth, *Diss. Abstr. Int.*, 36:736, 1975.
Zawisza et al., *Arch. Immunol. Ther. Exp.*, 29:235, 1981
What is claimed is:

1. A method of treating a host having a benign or malignant prostate carcinoma tumor, breast carcinoma tumor, or non-small cell lung carcinoma tumor, or a viral infection due to herpes virus or human immunodeficiency virus; the method comprising administering to the host a therapeutically effective amount of a compound having structure A, or an optical isomer thereof:

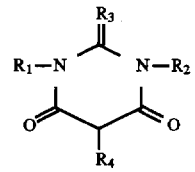

wherein
$R_1$ and $R_2$ are independently hydrogen, or alkyl, alkoxy, polyether, alkylhalide, hydroxyalkyl, alkylamine or alkylsulfhydryl having 1–6 carbon atoms, or aryl;
$R_3$ is O, S, Se or $C(CH_3)_2$; and
$R_4$ is hydrogen.

2. The method of claim 1 wherein $R_1$ and $R_2$ are alkyl.
3. The method of claim 1 wherein $R_3$ is O, or S.
4. The method of claim 1 wherein $R_1$ and $R_2$ are alkyl; and $R_3$ is O, or S.
5. The method of claim 1 where the host is a human host.
6. The method of claim 1 wherein the administering is ex vivo.
7. The method of claim 1 wherein the alkyl is butyl.
8. The method of claim 6 where the butyl is n-butyl.
9. The method of claim 1 wherein $R_3$ is S.
10. The method of claim 1 where the alkyl is n-butyl, and $R_3$ is S.
11. A method of treating a human patient having prostate carcinoma, breast carcinoma, non-small cell lung carcinoma, fibrosarcoma, Burkitt lymphoma or lymphocytic leukemia, the method comprising the step of administering to the human patient a therapeutically effective amount of a compound having the structure C1:

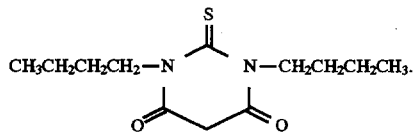

12. The method of claim 11 wherein the patient has lymphocytic leukemia and administering is ex vivo treatment of body tissue.
13. The method of claim 12 wherein the body tissue is bone marrow or blood.
14. A method of treating a human subject having a prostate carcinoma or a breast carcinoma, the method comprising the step of administering to the human subject a therapeutically effective amount of a compound having the structure C1:

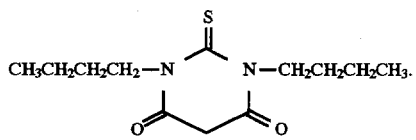

15. A method of treating a human subject having Burkitt lymphoma or lymphocytic leukemia, the method comprising the step of administering to the human subject a therapeutically effective amount of a compound having the structure C1:

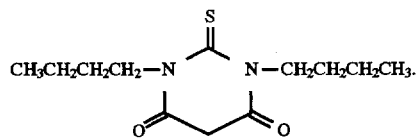
16. A method of treating a human subject having a viral infection due to herpes virus or human immunodeficiency virus, the method comprising the step of administering to the human subject a therapeutically effective amount of a compound having the structure C1:
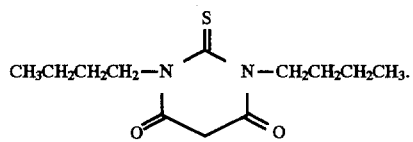
* * * * *

UNITED STATES PATENT AND TRADEMARK OFFICE
CERTIFICATE OF CORRECTION

PATENT NO. : 5,674,870

DATED : October 7, 1997

INVENTOR(S) : Kirpal S. Gulliya

It is certified that error appears in the above-identified patent and that said Letters Patent is hereby corrected as shown below:

In claim 8, column 20, line 30, delete "6" and substitute --7-- therefor.

In column 1, lines 5-6, delete "and a continuation of PCT/US96/01844 filed February 9, 1996."

Signed and Sealed this

Seventeenth Day of February, 1998

Attest:

BRUCE LEHMAN

Attesting Officer

Commissioner of Patents and Trademarks